United States Patent [19]

Ward

[11] Patent Number: 4,941,871
[45] Date of Patent: Jul. 17, 1990

[54] PREPARATION OF SYNTHETIC MATERIALS FOR IMPLANTATION IN MAMMALIAN TISSUE

[75] Inventor: Charles A. Ward, Toronto, Canada

[73] Assignee: HSC Research Development Corporation, Toronto, Canada

[21] Appl. No.: 236,147

[22] Filed: Aug. 25, 1988

[30] Foreign Application Priority Data

Sep. 25, 1987 [CA] Canada ................................. 547847

[51] Int. Cl.⁵ ............................ A61F 2/06; A61F 2/04
[52] U.S. Cl. ......................................... 600/36; 623/66; 264/344; 264/345
[58] Field of Search ............. 623/1, 66; 128/DIG. 22; 264/101, 102, 39, 233, 340, 344, 345; 600/36; 55/16, 80, 83–85

[56] References Cited

U.S. PATENT DOCUMENTS

| 4,164,524 | 8/1979 | Ward et al. | 128/DIG. 22 X |
| 4,265,927 | 5/1981 | Ericksson et al. | 623/1 X |
| 4,302,368 | 11/1981 | Dudley et al. | 623/66 X |
| 4,367,749 | 1/1983 | Dudley et al. | 128/637 |

FOREIGN PATENT DOCUMENTS 0092414 10/1983 European Pat. Off. ............. 600/36

Primary Examiner—Alan Cannon
Attorney, Agent, or Firm—Banner, Birch, McKie & Beckett

[57] ABSTRACT

A method for treating porous polytetrafluoroethylene and other types of synthetic materials having low surface tension to render the material suitable for use in bonding to living tissue. The synthetic material is enveloped with a liquid of sufficiently low surface tension to permit the liquid to enter the pores of the material. The liquid has a sufficiently low gas content to enable the liquid to absorb or displace essentially all gas nuclei held in the pores of the material as the liquid fills essentially all pores. After the low surface tension liquid has permeated all pores of the porous material, such liquid is replaced with a solution compatible with the body fluid and in which proteins have a low solubility to render the material suitable for implant. When such material is placed in contact with exposed tissue, an immediate bond is formed which permits implanting the material without the need of sutures to hold the material in place.

18 Claims, 3 Drawing Sheets

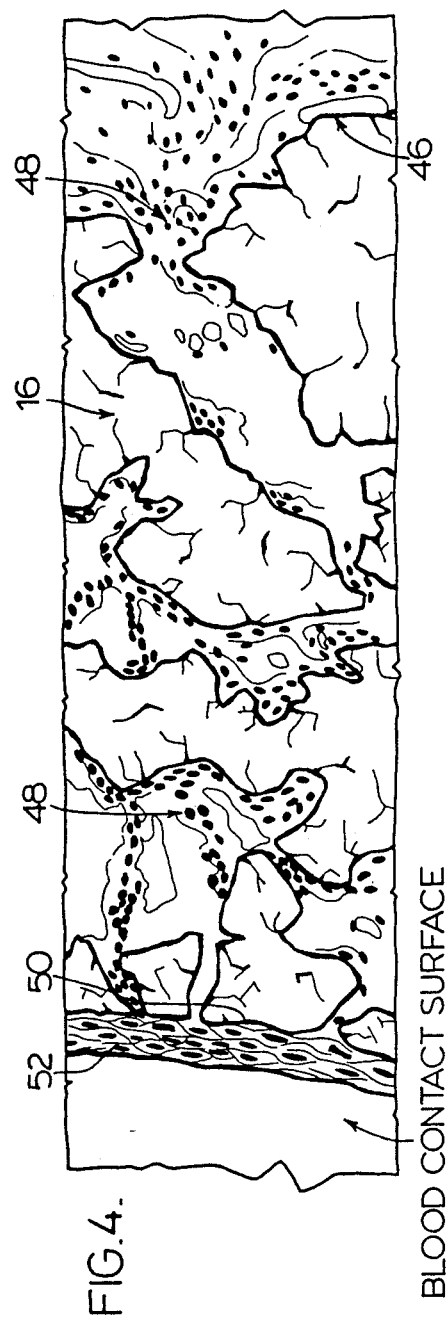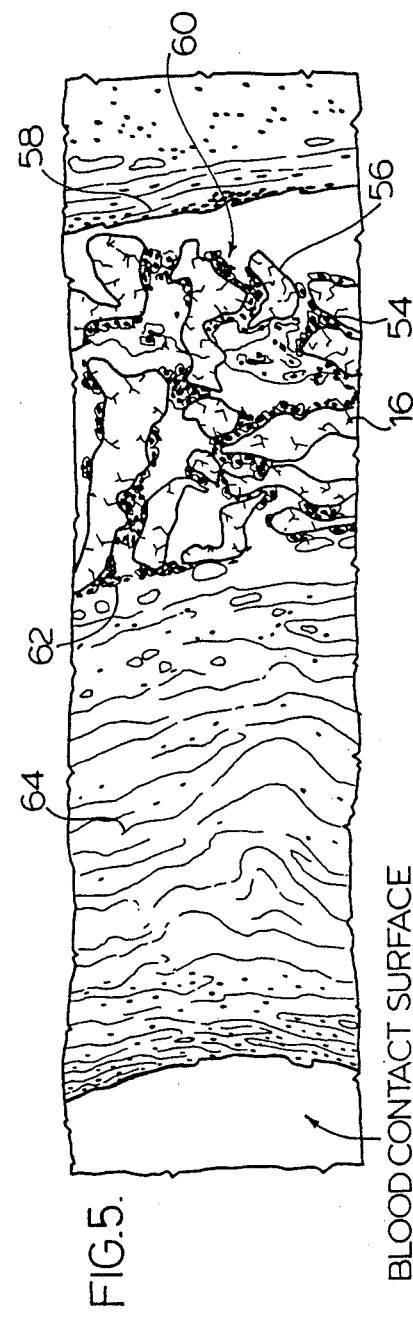

PREPARATION OF SYNTHETIC MATERIALS FOR IMPLANTATION IN MAMMALIAN TISSUE

FIELD OF THE INVENTION

This invention relates to treating synthetic materials so that the materials become suitable for use in contact with mammalian tissue and/or body fluids.

BACKGROUND OF THE INVENTION

Conventionally when natural mammalian tissue, such as blood vessels and bones must be replaced by synthetic materials, the synthetic material is put in place either with an adhesive or by suturing. There are many disadvantages with these practices. When a synthetic material is bonded to bone, for example, as is done in hip replacement, there is often failure of the adhesive bond. Synthetic materials sutured into place for purposes of replacing blood vessels tend to fail and leak at the suture. One reason for their failure is hyperplasia near the suture line. Thus causing the synthetic vessel to lose patency. Also thrombi tend to form at the surface lines, to come off, and to travel downstream thereby presenting a serious health hazard to the patient.

Moreover, at present there is no tubular material for blood vessel replacement that can be safely sutured in place as a means of replacing small diameter blood vessels, such as those found in the extremities of the body or in children. A small diameter (less than 6 mm) vessel replacement using presently available materials cannot be reliably implanted for a period of more than several months and expected to remain patent. Further, the period of time for which they remain patent diminishes as their diameter diminishes. This is thought to relate to the fact that gas nuclei are often trapped in the surface roughness of materials. As a result, the material activates the complement system of blood plasma and this enhances the adhesion and aggregation of both platelets and leukocytes and results in thrombus formation. As the diameter of the prosthesis diminishes, it is less and less tolerant of even any thrombus formation because of the danger of the prosthesis becoming occluded. It will also be appreciated that such adhesion could result in the formation of thrombi which can also be a serious health hazard to the patient.

Filling the inside volume of a tubular artificial vessel with saline is commonly done before the artificial artery is surgically placed in position. However, this does not remove the gas nuclei from the pores of the material, if the material has a low surface tension compared to the surface tension of the saline or phosphate solution. This situation would exist, for example, if expanded polytetrafluorethylene (PTFE) were exposed to an aqueous solution such as saline or phosphate buffer solution. When an artificial artery is prepared in this fashion for surgical implant, the gas nuclei give rise to the enhanced complement activation, cellular adhesion and thrombus formation referred to above.

In U.S. Pat. No. 4,164,524, a method and apparatus for treatment of the gas-permeable wall of certain types of medical tubing, which may be brought in contact with blood, is disclosed. This procedure removes the gas nuclei by contacting the synthetic material of the tubing with a blood-compatible solution on one side of the material and applying a vacuum to the other side of the synthetic material. However, this procedure cannot be used successfully to remove the air nuclei from certain materials that are otherwise potentially useful for artificial implants, such as arterial replacement. If this technique were to be applied to certain tubular materials suitable for replacement of arteries, such as expanded PTFE, the surface tension of the material would be considerably less than the surface tension of the saline priming solution. As a result, surface tension effects would prevent the priming solution from entering the pores of the material regardless of the extent of vacuum drawn. Thus, this method could not be used with advantage to prepare such a material for insertion into a blood vessel because it would not induce the priming fluid to enter the pores of the material. Immediately upon the vacuum being removed, the pores would refill with air and little advantage would have been gained from the priming procedure.

SUMMARY OF THE INVENTION

According to an aspect of the invention, a method for treating a porous synthetic material having pores extending therethrough to render the material suitable for use in bonding to living tissue comprises enveloping the material with a liquid of sufficiently low surface tension to permit the liquid to enter pores of the material. The liquid has a sufficiently low gas content to permit the liquid to remove essentially all gas nuclei held in the pores of the material. The liquid is induced to fill essentially all pores in the material and remove essentially all of the gas nuclei held in the pores. The liquid is replaced with an aqueous solution which is compatible with body fluid and in which proteins have a low solubility to provide the desired implantable synthetic material.

According to another aspect of the invention, a porous synthetic material suitable for body implant has an ability to bond to living tissue. The material comprises a low surface tension structure having a plurality of pores which are essentially free of any gas nuclei. The pores of the material are filled with an aqueous solution that is compatible with body fluids and tissues and in which proteins have minimal solubility.

According to another aspect of the invention, a method for implanting the material into mammalian tissue comprises contacting the material with exposed mammalian tissue to form a temporary bond at an interface of the tissue and material without suturing in place. Cell ingrowth occurs spontaneously at the interface of the bond to complete a permanent secure bond between the tissue and the material.

BRIEF DESCRIPTION OF THE DRAWINGS

Preferred embodiments of the invention are shown in the drawings wherein:

FIG. 4 is a drawing of a section through a living tissue implant of synthetic material which has been treated in accordance with this invention and implanted in the aorta of a rabbit for a period of months; and FIG. 5 was drawn from a photograph of a section through a living tissue implant of synthetic material which has not been treated in accordance with this invention and implanted in a similar manner and for approximately the same time.

DETAILED DESCRIPTION OF THE PREFERRED EMBODIMENTS

Figure 1:
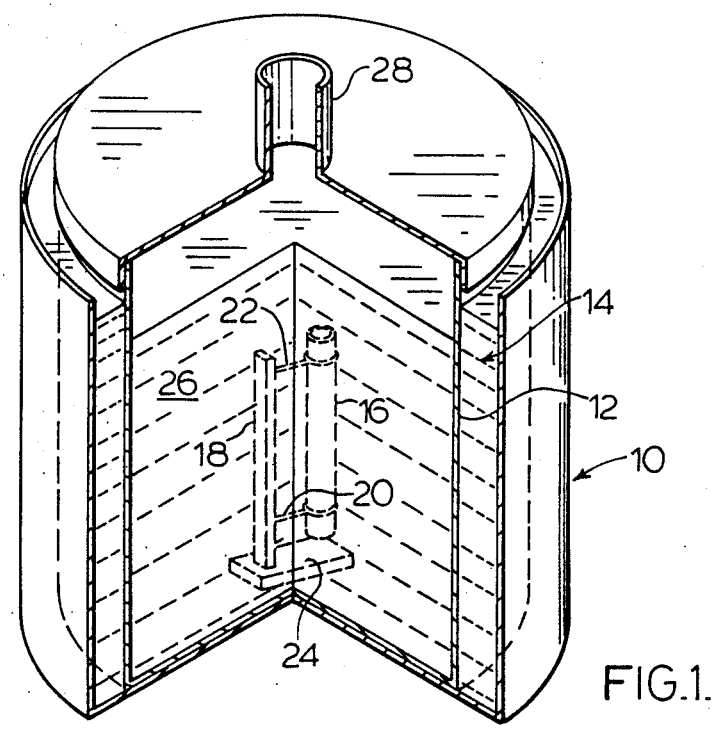
FIG. 1 is a section through a vessel containing a low surface tension liquid for removing gas nuclei from implantable material.

The present invention provides a porous synthetic material substantially free of gas nuclei, which allows bonding between the synthetic material and tissue, provided they are in intimate contact, and with time, allows rapid cell ingrowth to occur into the pores of the material. Thus, when used to replace a segment of an artery, the present invention can be relied on when desired to avoid the need for suturing the mammalian tissue, because the treated material forms almost immediately a suitable bond with the tissue and the bond subsequently becomes very strong. Also, the synthetic material of the present invention is more compatible with blood. When the material is brought into contact with the blood after being primed there is substantially less complement activation by the material as well as less platelet and leukocyte adhesion to the material. There is thus less cellular aggregation and less thrombus formation at the blood-contact surface of the material.

It is appreciated that a variety of implants are desired for correcting physical defects or damage caused by disease in a mammal. A preferred example of the manner in which the synthetic material may be used as an implant is an artificial blood vessel. The synthetic material is bonded to the mammalian tissue of a natural blood vessel where the body fluid carried through the synthetic material is blood. Hence, the solution used to fill the pores of the synthetic material to render it compatible with the mammalian fluids is a constituent which is blood compatible.

The surface tension of the low surface tension liquid is sufficiently low so that the contact angle between the low surface tension liquid and the surface of the synthetic material to be used is less than 90° and is preferably as near 0° as possible, i.e., it wets the material. This is preferably a contact angle in the range of 0° to 20°. The use of the term contact angle refers to the angle defined by intersecting surfaces of the liquid and solid material and measured in the liquid. In order to induce the liquid to enter the pores of the material, a pressure on the liquid may be developed which is greater than the sum of the vapor pressure of the low surface tension liquid and the tension of any absorbed gas in the low surface tension liquid. The process is aided if the contact angle is small, the dissolved gas content of the liquid is low, and the pressure under which the process takes place is large. Under these conditions, the low surface tension liquid will enter the pores of the material because the surface tension effect will force the gas trapped in the pores to be absorbed into the low surface tension liquid or to be displaced by the liquid.

The porous material preferably has a low surface energy (or surface tension) and is highly porous. The porosity can have a wide range, but the material must have structural integrity. Thus the porosity cannot be too high; nor can it be so low that cellular ingrowth cannot occur. Suitable materials include porous or expanded polytetrafluorethylene (PTFE), woven polyurethane and segmented polyurethane such as sold under the trademark BIOMER and a woven polymer fiber sold under the trademark DACRON. Porous PTFE is a particularly preferred material because of its low surface energy. The surface energy of the material is usually characterized by a high contact angle (in excess of 90°) when in contact with water.

The preferred low surface tension liquid is ethanol or acetone. Either of these liquids is preferably degassed as they tend to enter readily the pores of the synthetic material when the low surface tension liquid is degassed. Furthermore, the degassed liquid has an increased ability to absorb gas nuclei in the pores. When the material to be used for conduit replacement is expanded PTFE, a suitable low surface tension liquid would be degassed ethanol. When a liquid such as acetone is to be used as the low surface tension liquid, great care must be taken to ensure that it is thoroughly washed out of the synthetic material before it is implanted in a patient.

Suitable solutions compatible with body fluid depend on the type of mammalian tissue being bonded by the synthetic material and are readily apparent to one skilled in the art. Preferably, the solution is degassed. For an artificial artery, preferably a degassed physiological saline solution or a solution with a pH in the range which ensures a low solubility therein for plasma proteins. If the solubility of the plasma proteins in the fluid filling the pores is low, then these proteins will adhere to the inside surface of the pores and impede the diffusion of the plasma through the pores of the material. This will prevent the formation of a seroma on the outside of the artificial artery. This is particularly the case when saline is used as the body fluid compatible solution.

It is believed that the removal of the gas from the pores of the porous material and its replacement with the solution compatible with body fluid provides a suitable material for promoting cell ingrowth and in the case of blood vessels reduces both platelet and leukocyte adhesion, and prevents the formation of a seroma on the outside of the artificial vessel. The prior art method of adding only a blood-compatible solution to porous tubular polytetrafluoroethylene material for use as an artificial blood vessel does not remove many of the gas nuclei from the walls of the material. The contact angle between the surface of the material and the aqueous blood-compatible solution is well in excess of 90°; therefore, the blood-compatible solution cannot enter the pores of the material nor remove any of the gas nuclei trapped in the pores of the material. The present invention enhances the removal of the gas nuclei by initially bringing a low surface tension liquid, that is miscible with a physiological eluent, or rinse solution, in contact with the material, allowing the surface tension effects and vapor pressures to force it into the pores. The liquid with absorbed or dissolved gas nuclei is replaced by washing or eluting the low surface tension liquid from the pores of the synthetic material with a physiological eluent such as saline and thereby replacing the low surface tension liquid in the pores with the physiological solution.

In a preferred embodiment of the process, a PTFE material which has been expanded to form a porous structure is treated. Ethanol is placed in a vessel and then the PTFE tube is added. The vessel containing both the ethanol and the PTFE tube is then placed in a heated bath, brought to a temperature of greater than 37° C. A temperature of approximately 50° C. is often used. Then they are allowed to stand under this condition for several hours. This procedure effectively degasses the ethanol and allows it to enter the pores of the PTFE tube. The blood-compatible liquid that is to be used to wash out the ethanol is thoroughly degassed by exposing it to a vacuum for several hours while it is being stirred and heated to maintain its temperature at or near 37° C. After degassing, the vacuum is removed and its temperature is brought to the same as that of the ethanol. Then it is used to rinse slowly and thoroughly the ethanol from the vessel containing the porous PTFE tube. After the rinsing procedure, the synthetic material and the blood-compatible liquid are brought to 37° C.

Figure 2:
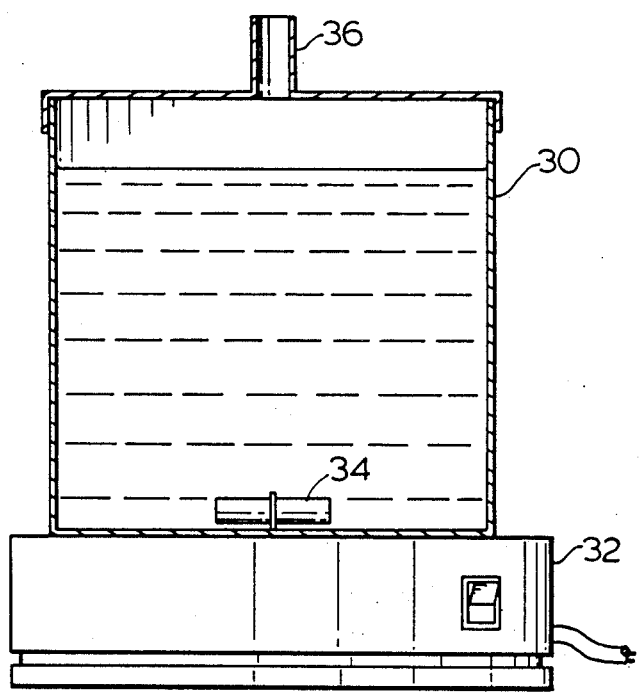
FIG. 2 is a section through a vessel used in preparing the aqueous physiological solution used in the final treatment of the implantable material.

The procedure for treating the implantable material will now be described with respect to the apparatus shown in FIGS. 1 through 3. In FIG. 1, a specially designed vessel 10 has an inner container 12 with a heat jacket defined by a bath solution held at a predetermined temperature. The implantable material 16, which is in the form of a small diameter vessel, is supported on a stand 18 having arms 20 and 22 which engage and support the implantable material 16. The stand 18 includes a base 24 which rests on the bottom of the container 12. The container 12 is filled with a low surface tension liquid 26. By immersing the implantable material 16 in the low surface tension liquid 26, the implantable material is enveloped by the low surface tension liquid to permit the liquid to permeate the porous implantable material and absorb or displace gas nuclei therein the manner previously discussed. In accordance with a preferred aspect of the invention, with the implantable material being PTFE, the preferred low surface tension liquid is ethanol. The ethanol may be heated to near but below its boiling temperature to degas the ethanol. A vacuum may be drawn at conduit 28 to ensure complete degassing of the ethanol. After the vacuum is removed, the bath solution 14 may be then adjusted to a temperature of approximately 50° C. The material is left in the ethanol bath for a period of a few hours to allow the removal by absorption of displacement of the gas nuclei from the pores of the implantable material by the ethanol.

It is understood that the low surface tension liquid has a greater capacity for absorbing gas nuclei at cooler temperatures. The concentration of gas in the ethanol at the higher temperature is lower, such as at boiling temperatures. However, the capacity of the ethanol to absorb gas increases as the ethanol is cooled down to 50° C. and even lower such as in the range of 37° C. Allowing the material to remain in the ethanol for a period of time will insure the complete removal of the gas nuclei from the implantable material. While the gas nuclei absorption is taking place, the conduit 28 may be simply vented to room air.

After the gas nuclei have been absorbed, or displaced by the ethanol, it is important to replace the ethanol with a physiologically compatible solution, such as saline. With reference to FIG. 2, a vessel 30 is mounted on a heating unit 32 with provision for magnetic stirrer 34. The outlet conduit 36 of the vessel is connected to a vacuum pump to draw a vacuum in the vessel 30. The selected physiologically compatible fluid, which may be for example saline, is placed in the container 30. The saline is heated to normal boiling point with vacuum drawn to completely degas the saline solution. In accordance with a preferred aspect of the invention, the ethanol should be replaced with a degassed physiological solution. Care must be taken to insure that the physiological parameter such as osmolarity is not changed by this process.

Figure 3:
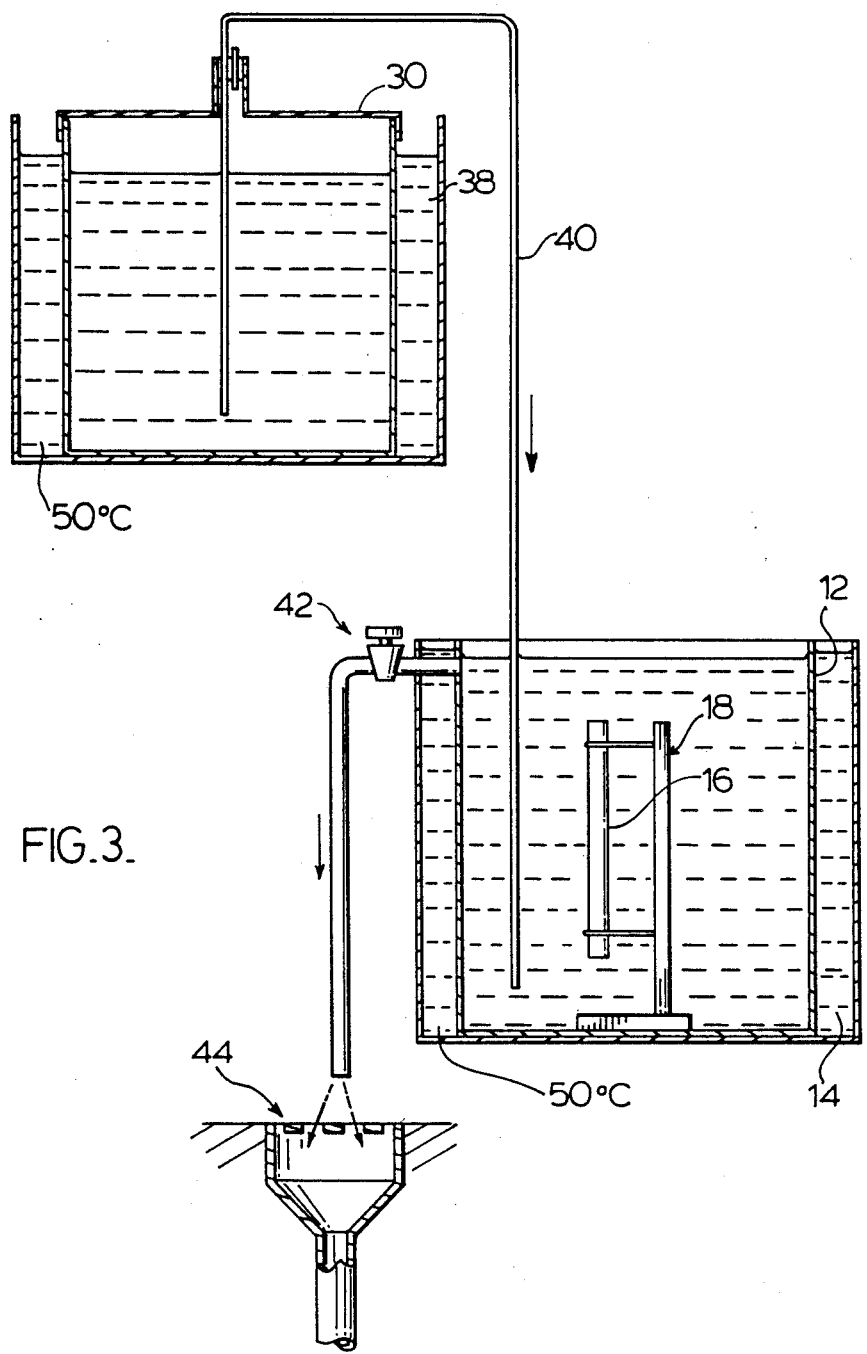
FIG. 3 is a section through the vessel system of FIG. 1 in combination with the vessel system of FIG. 2 for use in rinsing the low surface tension liquid from the implantable material.

As shown in FIG. 3, the container 12 is adapted to provide for continuous flow of the physiological fluid through the container to replace the ethanol. The bath fluid 14 holds the solution temperature at approximately 50° C. (the same temperature as the ethanol) during this process. A bath 38 is provided to maintain the saline solution at that temperature. A suitable pump (not shown) or by syphoning passes the saline solution through conduit 40 into the vessel 12. An overflow conduit 42 is provided to remove the solution from the container 12 at the rate that saline is introduced thereto. Conduit 42 is connected to a drain as indicated by arrow 44. With continuous circulation of saline through the container 12, eventually all ethanol in the implantable material 16 is replaced to complete the final phase of treatment of the implantable material for use. A final rinsing of the material is performed with the constant temperature baths brought to a temperature of 37° C. Depending upon the flow rates of the saline, the washing process in removing ethanol from the treated implantable material may continue for approximately two days.

The thus treated porous tubular material is then stored in a closed vessel filled with the blood-compatible liquid to avoid re-nucleation of the air nuclei in the pores of the expanded PTFE. It is then ready for use with a patient.

For example, it could be used to strengthen a portion of a natural artery that had been weakened for some reason and which is in danger of bursting at that point. After a segment of the tubular material has been prepared by the procedure described above, and the artery has been exposed using standard surgical procedures, it is clamped above and below the position where the insert is to be made. A small opening is made in the artery, and the prepared tubular material is inserted into the opening. The outer diameter of the prepared material should be slightly larger in diameter than the natural artery. The natural elasticity of the artery would allow this, and it would bring the inside surface of the artery into intimate contact with the outside surface of the prepared tubular material.

The tubular material should be inserted into the native artery above and below the opening made in the arterial wall. No suturing is necessary. The clamps are then released, allowing blood to flow through the inserted tubular material.

If the porous PTFE tube is to be used to by-pass a portion of the patient's natural artery, then after the artery is exposed and clamped using standard surgical procedures, a small opening is made in the patient's artery at each end of the section of artery that is to be by-passed. A small portion of the prepared porous PTFE tube is inserted into the opening made in the patient's artery. If the diameter of the patient's artery is approximately the same or slightly smaller than the outside diameter of the porous PTFE tube, then a natural bond will form immediately after the patient's natural artery and the prepared porous PTFE tube is brought in contact. The artery can be unclamped and this bond will prevent any leakage of blood from the artery. This bond eliminates the necessity of any suturing. Cell ingrowth begins almost immediately and by the end of a few weeks, provides a very strong bond. It is appreciated that a similar technique may be applied in grafting a prosthesis to bone. The prosthesis, for example, a hip joint replacement may be coated or have connected thereto a porous PTFE expanded material treated in accordance with this invention. The treated prosthesis may then be implanted in the bone tissue without the need for adhesives.

The porous PTFE tube can also be used in a manner that would obviate the need for suturing when replacing a heart valve. In this procedure, a valve is inserted inside the porous PTFE tube. If the PTFE tube is made slightly larger than the natural vessel into which it is placed, then an incision can be made in the vessel and the porous PTFE tube inserted. The natural vessel will then bond to the porous PTFE tube and eliminate the necessity for suturing the tube into place.

The invention will be further described with reference to the following Examples.

EXAMPLE 1

A 2 mm diameter, 4 cm long tube of PTFE which had been expanded to obtain a porous structure was washed in degassed ethanol by the procedure described above. The tube was subsequently washed with a degassed physiological saline until the ethanol had been almost completely removed from the pores of the PTFE material. This required approximately three hours of rinsing with approximately 2 liters of degassed physiological saline. The porous PTFE tube was then stored in degassed physiological saline at 37° C. until it was required for surgery. The aorta of a rabbit was then exposed using a standard surgical procedure, clamped, and a small incision made that allowed the PTFE tube to be inserted into the artery. After insertion of the porous tubular material, the clamp was removed and blood was allowed to flow through the PTFE tube. No suturing was necessary to prevent leakage of blood from the incision. The seal between the outer surface of the PTFE tube and natural artery was observed to be free of leakage. Subsequent investigation showed that cell ingrowth occurred along the outer surface of the PTFE material and that the natural artery was strongly bonded to the porous PTFE tube. A section through this material is illustrated in FIG. 4. The extensive cell ingrowth 48 about the outer surface 46 of the implant is shown which has established a permanent bond between tissue and PTFE without any need for suturing. The extensive cell growth 48 continues throughout the pores of the material down to the inner surface 50 of the implant 16. At the inner surface 50 which is in contact with the blood, a uniform layer of cellular growth 52 is formed to line the inner surface 50 of the implant to complete and form a normally healthy vessel. Such growth enhances the long term patency of the implant. The formation of the neo-intima cell layer 52 on the interior of blood contact surface of the PTFE implant demonstrates the blood compatibility of the contact surface.

EXAMPLE 2

A 2 mm diameter, 6 cm long porous PTFE tube was primed by the procedure described above so that ultimately the pores were filled with physiological saline. The porous PTFE tube was then stored in physiological saline at 37° C. without exposing it to air, until it was ready for use in by-passing a portion of the natural artery of a rabbit.

The aorta of a rabbit was exposed using a standard surgical procedure. The aorta was clamped and small incisions were made approximately 3 cm apart. Then approximately 1.5 cm of the PTFE tube was inserted into the aorta of the rabbit, leaving approximately 3 cm of the PTFE tube outside the aorta of the rabbit. The aorta was then unclamped and blood was allowed to flow through the PTFE tube. It was observed that no leakage took place at the incisions. The bond between the primed porous PTFE and the natural artery was sufficient to prevent any leakage and no sutures were used to maintain this condition. It was found that the patency of the arterial by-pass attached to the natural artery in this fashion was much better than the same type of material primed by the prior art method of only using physiological saline, and suturing the artificial vessel into position.

Further when the artificial artery was primed so as to remove the air nuclei from the pores and the pores were filled with physiological saline, it was found that no seroma formed on the outside of the synthetic material that was outside the natural artery.

EXAMPLE 3

When this same procedure was attempted without priming the PTFE so as to remove the gas nuclei from the pores of the material, it was found that a secure bond did not form between the PTFE material and the natural artery. The PTFE tube would not reliably remain in the incision without suturing. With reference to FIG. 5, the untreated material has separated from the tissue which is entirely unsatisfactory. To avoid confusion in comparing FIGS. 4 and 5, it is important to note that the section of FIG. 4 is considerably enlarged compared to FIG. 5. The untreated material 16 has minimal cell growth 54 in the pore structure. The cell growth 58, which is forming on the exterior 56 of the implant, is not connected to the porous material as evidenced by the gap 60. Furthermore, on the interior 62 of the implant, thrombus 64 has formed. Such thrombus on the interior of the implant tube has occurred to the extent that occlusion of the tube is about to occur. Clearly the untreated material firstly does not establish a secure bond with the outer tissue 58 and secondly, encourages the growth of thrombus on the interior to provide only short term patency of the implant. Hence even if suturing had been used to secure the implant in place, the thrombus growth would still result in short term patency. On the other hand, with the treated material of this invention, regardless of whether the implant is sutured in place, long term patency of the implant is assured due to the immediate acceptance by the living tissue cells which provide extension cell ingrowth in the porous materials.

Accordingly, when a porous material has been primed in accordance with this invention, so as to fill the pores with an aqueous solution that is compatible with body fluids and tissues thereby removing the gas nuclei from the pores of the material and the material is brought in contact with blood, there is less complement activation by the material. Cell growth into the pores of the synthetic material is promoted and a thin cellular layer forms on the blood contact surface. This cellular layer is more compatible with blood than the unprimed surface. Thus when a synthetic material is made into tubular form, primed as described, and used to replace an artery, the prosthesis has improved patency and segments of even small diameter arteries may be replaced by the primed material. The surgeon using this material now has the option of either suturing or not suturing the implant in place depending on the circumstances of use.

Although preferred embodiments of the invention have been described herein in detail, it will be understood by those skilled in the art that variations may be made thereto without departing from the spirit of the invention or the scope of the appended claims.

I claim:

1. A method for treating a porous synthetic material which has pores extending therethrough to render said material suitable for use in bonding to living tissue, said method comprising:

enveloping said material with a liquid of sufficiently low surface tension to permit said liquid to enter pores of said material, said liquid having a sufficiently low gas content to permit said liquid to remove essentially all the gas nuclei held in said pores of said material, heating said liquid to induce said liquid to fill essentially all pores in said material and absorb essentially of of said gas nuclei held in said pores, replacing essentially all of said liquid in said pores of said material with a solution which is compatible with body fluid and in which proteins have a low solubility.

2. A method of claim 1, wherein said material being treated has a low surface energy.

3. A method of claim 1, wherein said material being treated is porous polytetrafluoroethylene or woven polyurethane.

4. A method of claim 2, wherein a contact angle defined at an interface of said low surface tension liquid and said material is less than 90°.

5. A method of claim 1, wherein said solution is phosphate buffer solution or saline solution which is compatible with body fluids and tissue.

6. A method of claim 1, wherein said liquid is ethanol which is elevated to a temperature of approximately 37° C., said material being immersed in said liquid for an extended period until essentially all pores are filled with said liquid and gas nuclei trapped in said pores is absorbed by said liquid.

7. A method of claim 6, wherein said solution is heated to approximately 37° C., said solution being passed over said material to rinse said ethanol out of said pores until essentially all ethanol is replaced by said solution.

8. A method of claim 7, wherein said material having said pores filled with said solution is stored in said solution.

9. A method of claim 8, wherein said solution has been degassed, said material in said solution being stored in an air free sealed container.

10. A method of claim 1, wherein said material is in the shape of a tube.

11. A method of claim 10, wherein said tube is of small diameter in the range of 6 mm or less.

12. A method of claim 1 wherein said low surface tension liquid is ethanol or acetone.

13. A method for treating porous polytetrafluoroethylene or woven polyurethane which has pores extending therethrough to render said material suitable for use in bonding to living tissue, said method comprising:

enveloping said material with a liquid of sufficiently low surface tension to permit said liquid to enter pores of said material, said liquid having a sufficiently low gas content to permit said liquid to remove essentially all the gas nuclei held in said pores of said material, inducing said liquid to fill essentially all pores in said material and absorb essentially all of said gas nuclei held in said pores, replacing essentially all of said liquid in said pores of said material with a solution which is compatible with body fluid and in which proteins have a low solubility.

14. A method of claim 13, wherein said material being treated is porous polytetrfluoroethylene, a contact angle defined at an interface of said low surface tension liquid and said material is in the range of about 0° to 20°.

15. A method of claim 14, wherein said low surface tension liquid is ethanol or acetone.

16. A method of claim 15, wherein said liquid is ethanol.

17. A method of claim 15 or 16, wherein said low surface tension liquid is degassed prior to treating said material.

18. A method of claim 6, wherein said solution is degassed.

* * * * *